US011470826B2

(12) United States Patent
Tanaka et al.

(10) Patent No.: US 11,470,826 B2
(45) Date of Patent: Oct. 18, 2022

(54) METHOD OF CONVENIENTLY PRODUCING GENETICALLY MODIFIED NON-HUMAN MAMMAL WITH HIGH EFFICIENCY

(71) Applicant: National University Corporation Tokyo Medical and Dental University, Tokyo (JP)

(72) Inventors: Kohichi Tanaka, Tokyo (JP); Tomomi Aida, Tokyo (JP); Yusaku Wada, Atsugi (JP)

(73) Assignee: NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 412 days.

(21) Appl. No.: 15/527,085

(22) PCT Filed: Oct. 6, 2015

(86) PCT No.: PCT/JP2015/078259
§ 371 (c)(1),
(2) Date: May 16, 2017

(87) PCT Pub. No.: WO2016/080097
PCT Pub. Date: May 26, 2016

(65) Prior Publication Data
US 2017/0354130 A1    Dec. 14, 2017

(30) Foreign Application Priority Data

Nov. 17, 2014  (JP) .............................. JP2014-232963

(51) Int. Cl.
*A01K 67/027*    (2006.01)
*C12N 15/873*    (2010.01)
*C12N 15/11*    (2006.01)
*C12N 9/22*    (2006.01)
*C12N 15/90*    (2006.01)

(52) U.S. Cl.
CPC ............ *A01K 67/0278* (2013.01); *C12N 9/22* (2013.01); *C12N 15/11* (2013.01); *C12N 15/111* (2013.01); *C12N 15/873* (2013.01); *C12N 15/907* (2013.01); *A01K 2217/072* (2013.01); *A01K 2227/105* (2013.01); *A01K 2267/01* (2013.01); *C12N 2310/20* (2017.05); *C12N 2330/51* (2013.01)

(58) Field of Classification Search
USPC ........................ 800/18, 21; 530/350; 435/455
See application file for complete search history.

(56) References Cited

U.S. PATENT DOCUMENTS

2014/0170753 A1    6/2014 Zhang

FOREIGN PATENT DOCUMENTS

| WO | 2013/176772 | * 11/2013 |
| WO | WO 2013/188522 A2 | 12/2013 |
| WO | WO 2014/131833 A1 | 9/2014 |

OTHER PUBLICATIONS

International Search Report dated Dec. 28, 2015, in PCT/JP2015/078259.
Aida et al., "Cloning-free CRISPR/Cas system facilities functional cassette knock-in in mice," Genome Biology, Apr. 29, 2015, 16:87, 11 pages.
Aida et al., "Translating human genetics into mouse: The impact of ultra-rapid in vivo genome editing," Develop. Growth Differ., 2014, 56:34-45.
Aida et al., "Efficient Production of knock-in mice using CRISPR/Cas", The 4th Genome Editing Meeting, Oct. 6, 2014, Abstract, p. 8, with English translation, 1 page.
Aida et al., "In vivo genome editing for functional cassette knock-in mice using CRISPR/Cas," The 37th Annual Meeting of the Molecular Biology Society of Japan, On-line system for reviewing Abstract (http://www.aeplan.co.jp/mbsj2014/, Nov. 7, 2014, 3 pages, with English translation, 2 pages.
Jinek et al., "A Programmable Dual-RNA-Guided DNA Endonuclease in Adaptive Bacterial Immunity," Science, Aug. 17, 2012 (Epub Jun. 28, 2012), 337(6096):816-821, with 37 pages of Supplementary Materials.
Kim et al., "Highly efficient RNA-guided genome editing in human cells via delivery of purified Cas9 ribonucleoproteins," Genome Research, Jun. 2014 (Epub Apr. 2, 2014), 24(6):1012-1019, with 8 pages of Supplemental Materials.
Li et al., "Heritable gene targeting in the mouse and rat using a CRISPR-Cas system," Nature Biotechnology, Aug. 2013, 31(8):681-683.

(Continued)

*Primary Examiner* — Anne Marie S Wehbe
(74) *Attorney, Agent, or Firm* — Foley & Lardner LLP

(57) ABSTRACT

An object of the present invention is to provide a method of conveniently producing a genetically modified non-human mammal with high efficiency using a CRISPR-Cas9 system and particularly a production method whereby gene knock-in can be achieved with high efficiency regardless of the gene size. The method of producing a genetically modified non-human mammal comprises introducing a Cas9 protein, a crRNA fragment comprising a nucleotide sequence complementary to a target DNA region, and a tracrRNA fragment into a non-human mammalian oocyte to genetically modify the target DNA.

5 Claims, 6 Drawing Sheets

Specification includes a Sequence Listing.

(56) References Cited

OTHER PUBLICATIONS

Long et al., "Prevention of muscular dystrophy in mice by CRISPR/Cas9-mediated editing of germline DNA," Science, 2014, 345:1184-1188.
Shen et al., "Generation of gene-modified mice via CAS9/RNA-mediated gene targeting," Cell Research, 2013, 23:720-723.
Wang et al., "One-Step Generation of Mice Carrying Mutations in Multiple Genes by CRISPR/Cas-Mediated Genome Engineering," Cell, May 9, 2013, 153:910-918.
Wu et al., "Correction of a Genetic Disease in Mouse via Use of CRISPR-Cas9," Cell Stem Cell, Dec. 5, 2013, 13:659-662.
Yang et al., "One-Step Generation of Mice Carrying Reporter and Conditional Alleles by CRISPR/Cas-Mediated Genome Engineering," Cell, Sep. 12, 2013, 154:1370-1379.

\* cited by examiner

METHOD OF CONVENIENTLY PRODUCING GENETICALLY MODIFIED NON-HUMAN MAMMAL WITH HIGH EFFICIENCY

CROSS-REFERENCE TO RELATED APPLICATIONS

This application is a National Stage application of PCT/JP2015/078259, filed Oct. 6, 2015, which claims priority from Japanese application JP 2014-232963, filed Nov. 17, 2014.

TECHNICAL FIELD

The present invention relates to a method of conveniently producing a genetically modified non-human mammal using a CRISPR-Cas9 system with high efficiency and also relates to a production method whereby gene knock-in can be achieved with high efficiency.

BACKGROUND ART

Gene-targeted (knock-out or knock-in) mammals are important tools for analysis of gene functions in vivo. Production of gene-targeted mammals requires complicated and burdensome steps using embryonic stem cells (ES cells).

In recent years, the CRISPR-Cas9 (Clustered Regularly Interspaced Short Palindromic Repeat-associated protein 9) system has been developed and it has been gaining attention as a useful tool for genetic modification.

The CRISPR-Cas9 system is based on the acquired immunity mechanism in bacteria. The system allows a complex, comprising a Cas9 protein that is a double-strand DNA cleavage enzyme, RNA having a nucleotide sequence complementary to a target DNA region (crRNA), and RNA having a nucleotide sequence that is partially complementary to crRNA (trans-activating crRNA; tracrRNA), to specifically recognize and bind to a target DNA region for DNA cleavage.

Using this system, it is possible to produce a gene-targeted mammal by introducing RNA encoding the Cas9 protein, and the crRNA and the tracrRNA or a chimeric RNA having linked crRNA and tracrRNA, into a fertilized egg and directly manipulating the genome of the fertilized egg in vivo (in vivo genomic modification) without using ES cells (Patent Literature 1, Non-Patent Literature 1). Hitherto, production of knock-out mice (Patent Literature 2, Non-Patent Literatures 2-4) and production of knock-in mice having a single-nucleotide substitution (Non-Patent Literatures 3,5,6) have been conducted many times by the above technique.

Meanwhile, there are few reports on production of knock-in mammals into which a gene having relatively large size has been introduced using the CRISPR-Cas9 system. In addition, it is known that knock-in efficiency for genes of such larger size is very low (e.g., about 10%) (Non-Patent Literature 7). In other words, it is not easy to produce knock-in mammals into which a gene having relatively large size has been introduced using the CRISPR-Cas9 system.

CITATION LIST

Patent Literature

Patent Literature 1: WO2014/131833
Patent Literature 2: WO2013/188522

Non-Patent Literature

Non-Patent Literature 1: Aida, T. et al., Dev. Growth Differ. 56, 34-45, 194 (2014).
Non-Patent Literature 2: Shen, B. et al., Cell Res. 23 720-3 (2013)
Non-Patent Literature 3: Wang, H. et al., Cell 153, 910-8 (2013)
Non-Patent Literature 4: Li, D. et al., Nat. Biotechnol. 31, 681-3 (2013)
Non-Patent Literature 5: Long, C. et al., Science 345, 1184-8 (2014)
Non-Patent Literature 6: Wu, Y. et al., Cell Stem Cell 13, 659-62 (2013)
Non-Patent Literature 7: Yang, H. et al., Cell 154, 1370-9 (2013)

SUMMARY OF INVENTION

Technical Problem

An object of the present invention is to provide a method of conveniently producing a genetically modified non-human mammal with high efficiency using the CRISPR-Cas9 system and particularly a production method whereby gene knock-in can be achieved even for relatively large gene size with high efficiency.

Solution to Problem

As a result of intensive studies in order to solve the above problem, the present inventors found that target DNA can be genetically modified by introducing the Cas9 protein in the form of a protein but not RNA, together with a crRNA fragment and a tracrRNA fragment, into a fertilized egg, and that gene knock-in is possible even for relatively large gene size with high efficiency by such method, thereby making it possible to produce a genetically modified non-human mammal in a convenient manner with high efficiency. This has led to the completion of the present invention.

Specifically, the present invention comprises the following constituent features.

(1) A method of producing a genetically modified non-human mammal, wherein the method comprises introducing a Cas9 protein, a crRNA fragment comprising a nucleotide sequence complementary to a target DNA region, and a tracrRNA fragment into a non-human mammalian oocyte to genetically modify the target DNA.
(2) The method according to (1), wherein the non-human mammal is selected from a rodent.
(3) The method according to (1) or (2), wherein the oocyte is a fertilized egg.
(4) The method according to any one of (1) to (3), wherein the crRNA fragment comprises a nucleotide sequence complementary to a target DNA and the nucleotide sequence shown in SEQ ID NO: 2 or a mutant sequence thereof.
(5) The method according to any one of (1) to (4), wherein the tracrRNA fragment comprises the nucleotide sequence shown in SEQ ID NO: 4 or a mutant sequence thereof.
(6) The method according to any one of (1) to (5), wherein the Cas9 protein, the crRNA fragment, and the tracrRNA fragment form a complex.
(7) The method according to any one of (1) to (6), wherein genetic modification is insertion of a gene or a nucleotide sequence into the target DNA region, and wherein the method comprises introducing a donor DNA comprising the gene or the nucleotide sequence, together with the Cas9 protein, the crRNA fragment, and the tracrRNA fragment, into a non-human mammalian oocyte.

(8) The method according to any one of (1) to (7), wherein the crRNA fragment and the tracrRNA fragment are each used at a concentration of more than 0.002 pmol/μL based on 1 ng/μL Cas9 protein.

(9) A kit for genetically modifying a target DNA, comprising:

a crRNA fragment comprising a nucleotide sequence complementary to the target DNA and the nucleotide sequence shown in SEQ ID NO: 2 or a mutant sequence thereof, wherein the crRNA fragment consists of a nucleotide sequence of 42 nucleotides or less; and/or a tracrRNA fragment comprising the nucleotide sequence shown in SEQ ID NO: 4 or a mutant sequence thereof, wherein the tracrRNA fragment consists of a nucleotide sequence of 69 nucleotides or less.

(10) The kit according to (9), further comprising a Cas9 protein, and/or a donor DNA comprising a gene or a nucleotide sequence to be inserted into the target DNA region.

(11) A method of producing a mouse having a gene or a nucleotide sequence inserted into a target DNA region, wherein the method comprises introducing a Cas9 protein, a crRNA fragment comprising a nucleotide sequence complementary to a target DNA region, a tracrRNA fragment, and a donor DNA comprising the gene or the nucleotide sequence into a mouse oocyte to insert the gene or the nucleotide sequence into the target DNA region, wherein the crRNA fragment has a length of 30 to 42 nucleotides, wherein the tracrRNA fragment has a length of 24 to 69 nucleotides, wherein the Cas9 protein is used at a concentration of 30 ng/μL or more, and wherein the crRNA fragment and the tracrRNA fragment are each used at a concentration of 0.6 pmol/μL or more.

This description includes part or all of the content as disclosed in the description and/or drawings of Japanese Patent Application No. 2014-232963, which is a priority document of the present application.

Advantageous Effects of Invention

According to the present invention, it is possible to provide a method of conveniently producing a genetically modified non-human mammal with high efficiency using a CRISPR-Cas9 system and particularly a production method whereby gene knock-in can be achieved even for relatively large gene size with high efficiency.

BRIEF DESCRIPTION OF DRAWINGS

FIG. 3-1 is a graph showing in vitro digestion efficiency of target DNA by the combination of the Cas9 protein and the crRNA and tracrRNA fragments at different concentrations.

FIG. 3-2 is a graph showing in vitro digestion efficiency of target DNA by the combination of crRNA fragments with different nucleotide lengths (0 bp (none), 20 bp, 30 bp, 36 bp, 39 bp, or 42 bp) and the Cas9 protein and tracrRNA fragment.

DESCRIPTION OF EMBODIMENTS

1. Cas9 Protein

Figure 1:
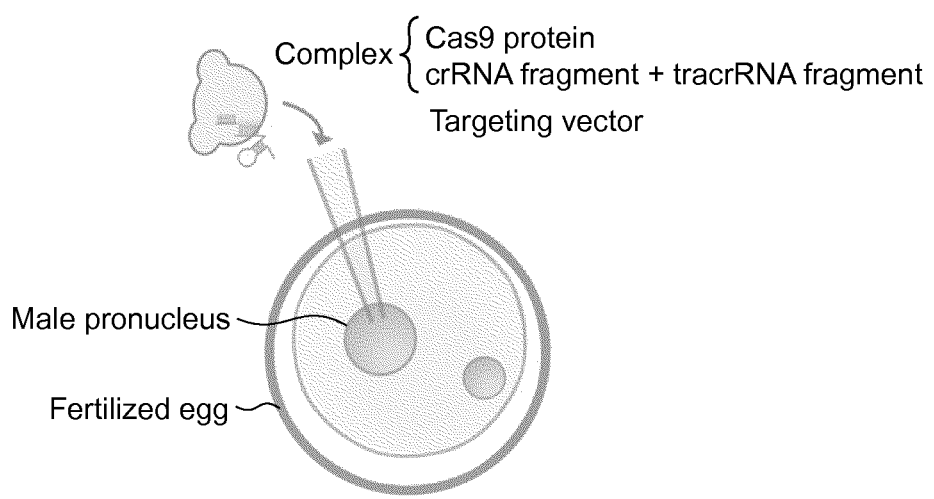
FIG. 1 illustrates the outline of the method of producing a genetically modified mouse according to the present invention. When the genetically modified mouse is a knock-in mouse, a targeting vector is used in combination.

In the present invention, any Cas9 protein may be used as long as it can be used in the CRISPR/Cas system, and it is not particularly limited as long as it binds to the tracrRNA and crRNA fragments described below to activate them so that target double-strand DNA can be cleaved. Such Cas9 proteins are known, and those disclosed in WO2014/131833 can be used. Preferably, the Cas9 protein from *Streptococcus pyogenes* may be used. The amino acid sequences and nucleotide sequences of Cas9 proteins are registered with known databases such as GenBank (http://www.ncbi.nlm.nih.gov) (e.g., Accession No.: Q99ZW2.1) and they can be used in the present invention.

Preferably, the Cas9 protein having the amino acid sequence shown in SEQ ID NO: 1 or consisting of the amino acid sequence can be used in the present invention. In addition, according to the present invention, the Cas9 protein may include an amino acid sequence having a deletion, substitution, addition, or insertion of one to several amino acids with respect to the amino acid sequence shown in SEQ ID NO: 1 or a polypeptide consisting of the amino acid sequence, as long as it retains the activity of the original protein, the activity of binding to the tracrRNA fragment and crRNA fragment described below to activate them so as to cleave target double-strand DNA. The expression "several" used herein means 1 to 50, preferably 1 to 30, and more preferably 1 to 10. Further, according to the present invention, the Cas9 protein may include an amino acid sequence having 80% or more, preferably 90% or more, more preferably 95% or more, and most preferably 99% or more sequence identity to the amino acid sequence shown in SEQ ID NO: 1 or a polypeptide consisting of the amino acid sequence, as long as it retains the activity of the original protein. Comparison of amino acid sequences can be made by known techniques, for example, using BLAST (Basic Local Alignment Search Tool at the National Center for Biological Information) or the like with the default setting.

In the present invention, the Cas9 protein is used in the form of protein. The Cas9 protein may be those produced by biological techniques including the production by transformed cells or microorganisms obtained by gene recombination techniques, or it may be chemically produced using routine peptide synthesis methods. Alternatively, a commercially available Cas9 protein may be used.

2. crRNA Fragment

In the present invention, the crRNA fragment includes at least a nucleotide sequence complementary to a target DNA region and a nucleotide sequence capable of interacting with a tracrRNA fragment from the 5'-side to 3'-side.

The term "target DNA region" refers to a region consisting of 17 to 30 nucleotides and preferably 17 to 20 nucleotides, which includes a site at which intended genetic modification of interest takes place on the genomic DNA of a non-human animal. Preferably, this region is selected from regions adjacent to "NGG (N denotes an arbitrary nucleotide)" (PAM (proto-spacer adjacent motif) sequence) on the 3' side.

A variety of methods are known as a method for selecting a target DNA region. For example, the region can be determined using the CRISPR Design Tool (http://crispr.mit.edu/) (Massachusetts Institute of Technology), E-CRISP (http://www.e-crisp.org/E-CRISP/), Zifit Targeter (http://zifit.partners.org/ZiFiT/) (Zing Finger Consortium), Cas9 design(http://cas9.cbi.pku.edu.cn/) (Peking University), CRISPRdirect (http://crispr.dbcls.jp/) (the University of Tokyo), CRISPR-P (http://cbi.hzau.edu.cn/crispr/) (Huazhong Agricultural University), Guide RNA Target Design Tool (https://wwws.blueheronbio.com/external/tools/gRNASrc.jsp) (Blue Heron Biotech), or the like.

The expression "nucleotide sequence capable of interacting with a tracrRNA fragment" refers to a nucleotide sequence that can bind (hybridize) to a partial nucleotide sequence of the tracrRNA fragment. Preferably, it includes at least the nucleotide sequence shown in SEQ ID NO: 2 in the present invention. Preferably, the nucleotide sequence capable of interacting with a tracrRNA fragment comprises or consists of a nucleotide sequence comprising the 1st to 10th, 11th, 12th, 13th, 14th, 15th, 16th, 17th, 18th, 19th, 20th, 21st, or 22nd nucleotide when the 5'-terminal guanine "G" is designated as the 1st nucleotide and the subsequent nucleotides are designated as the 2nd, 3rd, 4th, . . . and 22nd in the nucleotide sequence shown in SEQ ID NO: 3.

In the present invention, the nucleotide sequence capable of interacting with a tracrRNA fragment also includes an oligonucleotide, which has a nucleotide sequence that binds (hybridizes) to a nucleotide sequence complementary to the nucleotide sequence under stringent conditions and is capable of interacting with the tracrRNA fragment. The term "stringent conditions" refers to, for example, implementation of hybridization in the presence of 0.7 to 1.0 M NaCl at 65° C. and washing with a 0.1- to 2-fold concentration of SSC (Saline Sodium Citrate; 150 mM sodium chloride, 15 mM sodium citrate) solution at 65° C. (the same applies hereinafter). Such oligonucleotide may include an oligonucleotide consisting of a nucleotide sequence having an addition, substitution, deletion, or insertion of several nucleotides with respect to the nucleotide sequence (the term "several nucleotides" used herein refers to no more than 3 nucleotides or no more than 2 nucleotides), or an oligonucleotide consisting of a nucleotide sequence having 80% or more, more preferably 90% or more, most preferably 95% or more identity to the above nucleotide sequence when calculated using BLAST (e.g., with a default or initial setting parameters) or the like. Such oligonucleotide may be referred to herein as a "mutant sequence" of the above nucleotide sequence.

The crRNA fragment includes the nucleotide sequence complementary to a target DNA region and the nucleotide sequence capable of interacting with a tracrRNA fragment, and the crRNA fragment as a whole can be preferably 42 nucleotides or less, 39 nucleotides or less, or 36 nucleotides or less; or it can be 30 nucleotides or more, 36 nucleotides or more, or 39 nucleotides or more; for example, it can be 30 to 42 nucleotides, more specifically 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides, or 42 nucleotides.

The crRNA fragment can be chemically synthesized using a method known in the art as an oligonucleotide synthesis method, for example, the phosphotriethyl method, the phosphodiester method, or the like, or using a generally available automatic RNA synthesizer.

The crRNA fragment of the present invention may include a plurality types of crRNA fragments each having a different target DNA region, that is to say, having a different nucleotide sequence complementary to a target DNA region.

3. tracrRNA Fragment

In the present invention, the tracrRNA fragment has a nucleotide sequence on the 5' side, capable of binding (hybridizing) to a partial nucleotide sequence of the crRNA fragment, so that a crRNA fragment/tracrRNA fragment hybrid is formed via interaction between these nucleotide sequences. The hybrid functions to guide a Cas9 protein to a target DNA region.

In the present invention, the tracrRNA fragment is not particularly limited as long as it can guide the Cas9 protein, together with the crRNA fragment. However, it is preferable to use tracrRNA from *Streptococcus pyogenes*.

The nucleotide sequence of the tracrRNA fragment required for the CRISPR/Cas system has been elucidated to some extent (Jinek et al., Science 337: 816, 2012), and such findings can be used in the present invention. The tracrRNA fragment of the present invention includes at least the nucleotide sequence shown in SEQ ID NO: 4. Preferably, the tracrRNA fragment comprises or consists of a nucleotide sequence consisting of one nucleotide or a plurality of consecutive nucleotides selected from the 1st to 10th and/or the 35th to 69th nucleotides for nucleotides adjacent to 11th and/or 34th nucleotides, together with a nucleotide sequence consisting of the 11th to 34th nucleotides, when the 5'-terminal adenine "A" is designated as the 1st nucleotide and the subsequent nucleotides are sequentially numbered as the 2nd, 3rd, 4th, . . . and 69th in the nucleotide sequence shown in SEQ ID NO: 5.

Therefore, the tracrRNA fragment as a whole may comprise preferably 69 nucleotides or less, 59 nucleotides or less, 34 nucleotides or less; or 24 nucleotides or more, which is, for example, 24 nucleotides, 24 to 34 nucleotides, 24 to 59 nucleotides, or 24 to 69 nucleotides.

In the present invention, the tracrRNA fragment also includes an oligonucleotide, which has a nucleotide sequence capable of binding (hybridizing) to a nucleotide sequence complementary to the above nucleotide sequence under stringent conditions and can guide the Cas9 protein, together with the crRNA fragment. Examples of such oligonucleotides may include an oligonucleotide consisting of a nucleotide sequence having an addition, substitution, deletion, or insertion of several nucleotides with respect to the above nucleotide sequence (the term "several nucleotides" used herein refers to no more than 3 nucleotides or no more than 2 nucleotides), and an oligonucleotide consisting of a nucleotide sequence having 80% or more, more preferably 90% or more, and most preferably 95% or more identity to the above nucleotide sequence when calculated using BLAST (e.g., with a default or initial setting parameters) or the like. Such oligonucleotide may be referred to herein as a "mutant sequence" of the above nucleotide sequence.

The tracrRNA fragment can be chemically synthesized using a method known in the art as an oligonucleotide synthesis method, for example, the phosphotriethyl method, the phosphodiester method, or the like, or using a generally available automatic RNA synthesizer.

4. Donor DNA

In the present invention, the donor DNA is used in order to insert (knock-in) a desired gene or nucleotide sequence into a target DNA region via homologous recombination (HR) which takes place at a site of cleavage with the Cas9 protein.

The donor DNA includes two nucleotide sequences (so-called homology arms) having high identity to the nucleotide sequence in the target DNA region and a gene or a nucleotide sequence to be inserted, which is arranged between the two homology arms.

The homology arms are not particularly limited as long as they have sizes sufficient for implementation of homologous recombination. For example, they can be independently selected from those ranging from 0.5 to 10 kb.

In addition, the homology arms are not particularly limited as long as they have identity with the nucleotide sequence in the target DNA region to an extent sufficient for implementation of homologous recombination. Each arm may have 95% or more, preferably 97% or more, more preferably 99% or more, and even more preferably 99.9% or more identity when calculated using BLAST or the like (e.g., with a default or initial setting parameters).

The gene or the nucleotide sequence to be inserted may be an endogenous, exogenous, homologous, or heterologous with respect to an oocyte used in the method of the present invention.

The size of the gene or the nucleotide sequence to be inserted is not particularly limited, and those having various sizes may be used. Compared with conventional genes inserted using the CRISPR/Cas system, genes or nucleotide sequences having larger sizes, for example, those of 100 bp or more, 300 bp or more, 500 bp or more, 700 bp or more, 900 bp or more, 1 kb or more, 1.5 kb or more, 2 kb or more, 3 kb or more, 4 kb or more, or even 5 kb or more may be used.

A promoter and/or other control sequences can be operably linked to the gene or the nucleotide sequence to be inserted. The expression "operably linked" means that the inserted gene or nucleotide sequence is expressed in cells under the control of the promoter and/or other control sequences. Promoters and/or other control sequences are not particularly limited, and may be selected appropriately from constitutive promoters, tissue-specific promoters, stage-specific promoters, inducible promoters, and a CMV promoter, and other regulatory elements (e.g., a terminator sequence).

In the case of using a plurality types of crRNA fragments each having a different target DNA region, the donor DNA of the present invention may include a plurality types of donor DNAs each having homology arms corresponding to the plurality types of target DNA regions. In addition, genes or nucleotide sequences to be inserted, which are included in the plurality types of donor DNAs, may be different genes or nucleotide sequences.

The donor DNA may be described herein as a targeting vector, and these terms may be used interchangeably.

5. Method of Producing a Genetically Modified Non-Human Animal

The method of producing a genetically modified non-human mammal of the present invention comprises introducing the Cas9 protein, the crRNA fragment, and the tracrRNA fragment into a non-human mammalian oocyte to genetically modify a target DNA.

The term "non-human mammal" refers to a mammal other than a human, such as a non-human primate (e.g., monkey), cattle, horse, pig, sheep, goat, dog, cat, rat, or a mouse. Preferably, the non-human mammal is a rodent, and can be selected from a mouse, a rat, a guinea pig, a hamster, a rabbit, and the like. Particularly preferably the mammal is a mouse.

As the "oocyte," an oocyte before or after fertilization can be used. It is preferably an oocyte after fertilization, a fertilized egg. Particularly preferably, a fertilized egg is a pronucleus-stage embryo. A cryopreserved oocyte can be thawed and used.

The Cas9 protein, the crRNA fragment, and the tracrRNA fragment can be introduced into an oocyte using the microinjection method that is generally used for introducing a nucleic acid and/or a protein into an oocyte (Nagy A, Gertsenstein M, Vintersten K, Behringer R., 2003, Manipulating the Mouse Embryo. Cold Spring Harbour, N.Y.: Cold Spring Harbour Laboratory Press).

Microinjection may be conducted to the pronucleus of an oocyte, and to the female and/or male pronucleus, preferably male pronucleus of a fertilized egg.

The injection solution may comprise the Cas9 protein, the crRNA fragment, and the tracrRNA fragment at concentrations selected from one of or a plurality of the concentrations described in (i) to (iii) below:

(i) the concentration of the Cas9 protein is set to 5 to 5000 ng/µL, preferably 5 to 500 ng/µL, more preferably 10 to 50 ng/µL, even more preferably 20 to 40 ng/µL, and furthermore preferably 30 ng/µL;

(ii) the concentration of the crRNA fragment and the concentration of the tracrRNA fragment are each set above 0.002 pmol/µL, preferably 0.005 pmol/µL or more, more preferably 0.01 pmol/µL or more, and further preferably 0.02 pmol/µL based on 1 ng/µL Cas9 protein, and the upper limit of each concentration is 2 pmol/µL or less and preferably 0.2 pmol/µL or less (the concentration of the crRNA fragment and the concentration of the tracrRNA fragment may be the same or different); and (iii) the concentrations of the crRNA fragment and the tracrRNA fragment are each set above 0.06 pmol/µL, preferably 0.15 pmol/µL or more, more preferably 0.3 pmol/µL or more, and further preferably 0.6 pmol/µL or more, and the upper limit thereof is set to 60 pmol/µL or less and preferably 6 pmol/µL or less (the concentration of the crRNA fragment and the concentration of the tracrRNA fragment may be the same or different).

In one embodiment, the injection solution may contain 20 to 40 ng/µL and preferably 30 ng/µL of the Cas9 protein; 0.15 pmol/µL or more, preferably 0.3 pmol/µL or more, and more preferably 0.6 pmol/µL or more of the crRNA fragment; and 0.15 pmol/µL or more, preferably 0.3 pmol/µL or more, and more preferably 0.6 pmol/µL or more of the tracrRNA fragment.

The Cas9 protein, the crRNA fragment, and the tracrRNA fragment may preferably form a complex at the time of microinjection. The complex can be formed by incubating the injection solution containing the Cas9 protein, the crRNA fragment, and the tracrRNA fragment at 35° C. to 40° C., preferably 37° C. for at least about 15 minutes. This allows the formation of crRNA fragment/tracrRNA fragment hybrid through interaction between complementary nucleotide sequences, resulting in the formation of a complex in which the Cas9 protein is bound to the hybrid.

The injection amount of the injection solution may be an amount that is generally used for microinjection into an oocyte. In the case of microinjection into the pronucleus, the amount can be set to an amount with which enlargement of the pronucleus reaches a saturation level.

The injected Cas9 protein is guided by the crRNA fragment/tracrRNA fragment hybrid to a target DNA region on genomic DNA of a non-human animal so as to cause cleavage of double-strand DNA in the region, which results in genetic modification through non-homologous end joining (NHEJ) or homologous recombination (HR).

Non-homologous end joining may cause incidental insertion or deletion of nucleotides with high frequency at the cleavage site, leading to a frameshift mutation that results in disruption of the gene in the target DNA region (gene knock-out).

In the case of homologous recombination, homologous recombination takes place in the presence of the donor DNA as a template, which may result in insertion of a desired gene or nucleotide sequence included in the donor DNA into the target DNA region (gene knock-in). The donor DNA can be injected, together with the Cas9 protein, the crRNA fragment and the tracrRNA fragment, into an oocyte. The donor DNA may be contained, together with other components, at a concentration of 1 to 30 ng/µL, preferably 5 to 15 ng/µL, and more preferably 10 ng/µL in the injection solution.

More than one genetic modifications can be induced using the combination of the plurality types of crRNA fragments and the plurality of types of donor DNAs described above.

FIG. 1 shows one embodiment of microinjection according to the method of the present invention.

The microinjected oocyte may be implanted in the uterus of a pseudopregnant female non-human mammal, and littermates of the mammal may be obtained. Implantation can be performed using a fertilized egg of a 1-cell stage embryo, a 2-cell stage embryo, a 4-cell stage embryo, a 8-cell stage embryo, a 16-cell stage embryo, or a morula. The microinjected oocyte can be cultured under suitable conditions, if needed, until implantation. Implantation and culture of the oocyte can be carried out according to conventionally known techniques (see Nagy A et al. ibid.).

The presence or absence of genetic modification can be confirmed and the genotype can be determined based on conventionally known techniques. For example, PCR method, sequencing method, Southern blotting method, and the like can be used. Genomic DNAs subjected to such analyses may be extracted from a part of an embryo before implantation or from obtained animals.

According to the method of the present invention, it is possible to genetically modify a target DNA with high efficiency by introducing the Cas9 protein, the crRNA fragment, and the tracrRNA fragment into a non-human mammalian oocyte. In particular, it is possible to knock-in genes having various sizes (even genes having sizes relatively larger than those of genes conventionally introduced) with high efficiency (at, for example, 10% or more, 20% or more, 30% or more, 40% or more, 45% or more, or a higher percentage), when used in combination with the donor DNA. Thus, a genetically modified non-human mammal can be efficiently produced. In addition, according to the method of the present invention, a non-human mammal having a homozygous or heterozygous genetic modification can be produced. Therefore, it is possible to obtain a genetically modified non-human mammal having a desired genotype at an earlier stage (e.g., about 1 month for mice) compared to the conventional method using ES cells.

6. Kit for Genetically Modifying a Target DNA

The kit of the present invention comprises the crRNA fragment and/or the tracrRNA fragment, and as described above, it can be used for genetically modifying a target DNA and/or producing a non-human mammal whose target DNA is genetically modified.

The kit of the present invention may further comprises the Cas9 protein and/or the donor DNA.

Each element contained in the kit may be housed in a separate container or in the same container. Each element may be housed in an amount for single-time use in a container or in divided amounts in the same container (so that a user can take each element in an amount necessary for single-time use). Each element may be housed in a dry form in a container or it may be housed in a dissolved form in an appropriate solvent.

EXAMPLES

The present invention is specifically described with reference to the Examples below; however, the present invention is not limited thereto.

[Materials and Method]
(Targeting Vector)

A targeting vector was prepared using a pAAV-TetO-FLEX-HA-mKate2-TeNT-polyA plasmid (donated by Dr. Akihiro Yamanaka, Department of Neuroscience II, Research Institute of Environmental Medicine, Nagoya University) in the following manner. Firstly, the plasmid was digested with XhoI (NEB) and HindIII (NEB) so as to remove HA-mKate2-TeNT for inverse substitution/insertion of a PCR-amplified gene encoding EGFP. Secondly, the resulting product was digested with NarI (NEB) and BstEII (NEB) so as to remove AAV2-ITR for substitution/insertion of a fragment of the PCR-amplified β-actin (hereinafter referred to as "Actb") gene from genomic DNA of a C57BL/6J mouse (2.0 kb) as a left homology arm, using the In-Fusion HD Cloning Kit (Takara). Lastly, the resulting product was digested with NotI (NEB) and MluI (NEB) for substitution/insertion of a fragment of the PCR-amplified Actb gene from genomic DNA of a C57BL/6J mouse (2.0 kb) as a right homology arm via the In-Fusion reaction.

Figure 2:
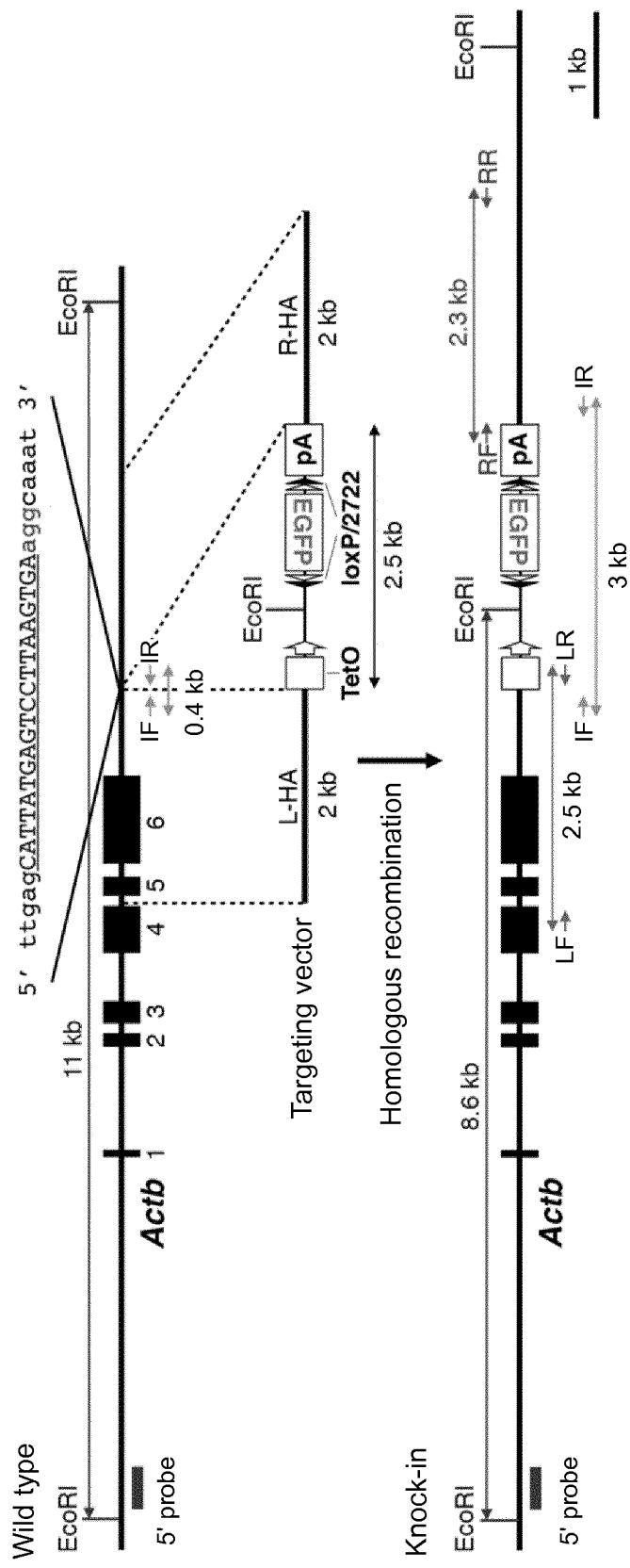
FIG. 2 schematically shows a "pActb-TetO-FLEX-EGFP-polyA" targeting vector and the outline of homologous recombination using the targeting vector.

The obtained targeting vector is hereinafter referred to as "pActb-TetO-FLEX-EGFP-polyA." FIG. 2 schematically illustrates the structure of pActb-TetO-FLEX-EGFP-polyA.

(Cas9 Protein)

A recombinant Cas9 protein was purchased from NEB and PNA Bio.

(crRNA Fragment and tracrRNA Fragment)

The tracrRNA fragment and the crRNA fragment having the nucleotide sequences shown in Table 1 below were chemically synthesized and purified via polyacrylamide gel electrophoresis (FASMAC Co., Ltd.). The crRNA fragment contains an Actb target sequence.

TABLE 1

| tracrRNA fragment (69 bp) | 5'-AAACAGCAUAGCAAGUUAAAAU AAGGCUAGUCCGUUAUCAACUUGAA AAAGUGGCACCGAGUCGGUGCU-3' | SEQ ID NO: 5 |
|---|---|---|
| crRNA fragment (42 bp) | 5'-cauuaugaguccuuaagugaGU UUUAGAGCUAUGCUGUUUUG-3' (each lower-case letter denotes a nucleotide sequence of target Actb) | SEQ ID NO: 6 |

(In Vitro Digestion Assay)
1. Examination of Concentration

The Cas9 protein (30 ng/µL), and the crRNA fragment and tracrRNA fragment (each at a concentration of 0 pmol/µL, 0.061 pmol/µL, 0.153 pmol/µL, 0.305 pmol/µL, or 0.61 pmol/µL) were incubated, together with the PCR product containing the Actb target sequence, in a Cas9 Nuclease Reaction buffer (NEB) at 37° C. for 60 minutes. Then, the mixture was treated with RNase A (5 mg) (at 37° C. for 30 minutes) to remove RNA. The reaction was terminated using a 6×DNA loading buffer containing 30% glycerol, 1.2%

SDS, and 250 mM EDTA, and then subjected to 2% agarose gel electrophoresis. The crRNA fragment and the tracrRNA fragment were not added to the control.

2. Examination of crRNA Fragment Length

In vitro digestion assay was conducted under the same conditions except that the crRNA fragment used in the experiment in 1 above was replaced by any of crRNA fragments having the nucleotide sequences listed in Table 2 below at 0.61 pmol/μL. None of the crRNA fragments was added to the control.

The term "crRNA fragment" refers to a fragment consisting of the nucleotide sequence shown in SEQ ID NO: 6, unless otherwise specified.

TABLE 2

| | crRNA fragment (each lower-case letter denotes a nucleotide sequence of target Actb) | |
|---|---|---|
| (42 bp) | 5'-cauuaugaguccuuaagugaG UUUUAGAGCUAUGCUGUUUUG-3' | SEQ ID NO: 6 |
| (39 bp) | 5'-cauuaugaguccuuaagugaG UUUUAGAGCUAUGCUGUU-3' | SEQ ID NO: 7 |
| (36 bp) | 5'-cauuaugaguccuuaagugaG UUUUAGAGCUAUGCU-3' | SEQ ID NO: 8 |
| (30 bp) | 5'-cauuaugaguccuuaagugaG UUUUAGAGC-3' | SEQ ID NO: 9 |
| (20 bp) | 5'-cauuaugaguccuuaaguga-3' | SEQ ID NO: 10 |

(Preparation of a Knock-in Mouse)

The Cas9 protein (30 ng/μL), the crRNA fragment (0.061 or 0.61 pmol/μL), the tracrRNA fragment (0.061 or 0.61 pmol/μL), and pActb-TetO-FLEX-EGFP-polyA (10 ng/μL) were added to 0.1 TE buffer, mixed, and incubated at 37° C. for at least 15 minutes. Thus, a complex was formed.

The 1-cell stage embryo used herein was obtained by crossing BDF1 mice (CLEA Japan, Inc.) and cryopreserved before use.

The above complex was microinjected into a male pronucleus of the thawed embryo and incubated at 37° C. for 24 hours. Then, a 2-cell stage embryo was implanted into an ICR pseudopregnant female mouse (CLEA Japan, Inc.), and littermates were obtained. Knock-in mice were screened for among the obtained littermates.

(PCR Screening)

A part of the tail of each littermate was collected and treated with proteinase K. Then, genomic DNA was prepared by the phenol extraction method. Subsequently, PCR was performed using the obtained genomic DNA as a template, ExTaq (Takara), and the three different pairs of primers listed in Table 3 below, followed by 1% agarose gel electrophoresis to screen for knock-in mice. The obtained PCR products were also cloned using a TOPO TA Cloning Kit (Life Technologies) and sequenced.

TABLE 3

| Primer | Sequence | SEQ ID NO. |
|---|---|---|
| IF | 5'-TGCAGAGAACACTGGTTGGT-3' | SEQ ID NO: 11 |
| IR | 5'-CAAGCTAACCTCAGCCTTGC-3' | SEQ ID NO: 12 |
| LF | 5'-TCCCTGGAGAAGAGCTATGA-3' | SEQ ID NO: 13 |
| LR | 5'-TATAGGCCTCCCACCGTACA-3' | SEQ ID NO: 14 |

TABLE 3-continued

| Primer | Sequence | SEQ ID NO. |
|---|---|---|
| RF | 5'-GAGTGCAGTGGCACAATCTT-3' | SEQ ID NO: 15 |
| RR | 5'-CCAGATGCCTTCTGTTGCATGCTT-3' | SEQ ID NO: 16 |

The position of each primer is shown in FIG. 2.

Southern Blotting

A Southern probe (0.8 kb) was prepared by PCR-amplifying BDF1 genomic DNA, cloning the amplification product using a TOPO TA Cloning Kit, and labeling the clone with a $^{32}P$ random primer (Perkin Elmer). The genomic DNA obtained from the knock-in mice was digested with EcoRI, separated via 0.8% agarose gel electrophoresis, transferred to a nylon membrane (Amersham), and hybridized with the Southern probe for detection, thereby confirming the genotype. FIG. 2 shows the positions of the probes.

(Primary Culture of Fibroblasts)

A small piece was cut out from an ear of each of 2-week-old mice, followed by treatment at 37° C. for 30 minutes using 4 mg/ml collagenase L (Nitta Gelatin Inc.) and 4 mg/ml dispase. The resulting product was cultured in 10% FBS/DMEM at 37° C. in 10% $CO_2$ for several days. The cultured cells were cotransfected with pCAG-Cre, pCMV-tTA (Takara), and pCMV-DsRed (Takara), using Lipofectamme® LTX & Plus reagent (Life Technologies). EGFP expression was confirmed using a fluorescence microscope.

[Results]

(In Vitro Digestion Assay)

1. Results of Examination of the Concentration

Figures 1, 3:
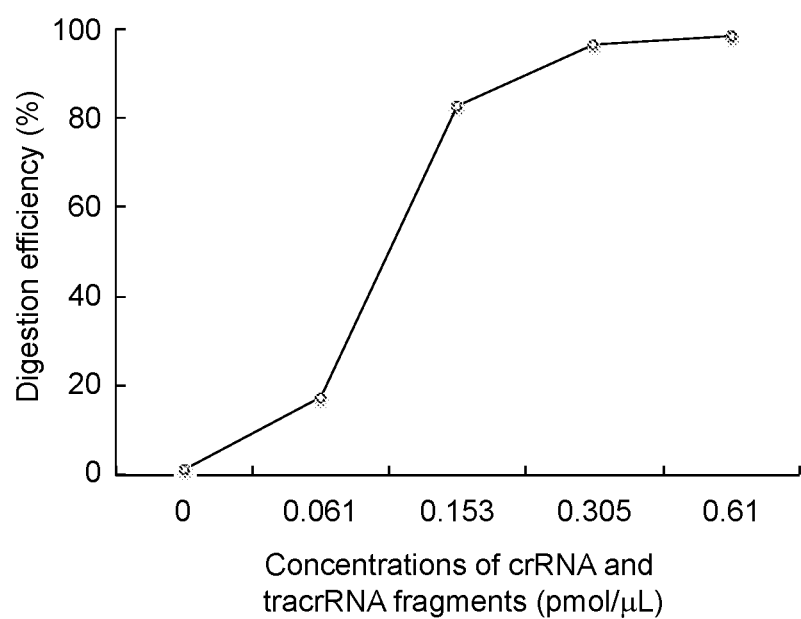
Figures 2, 3:
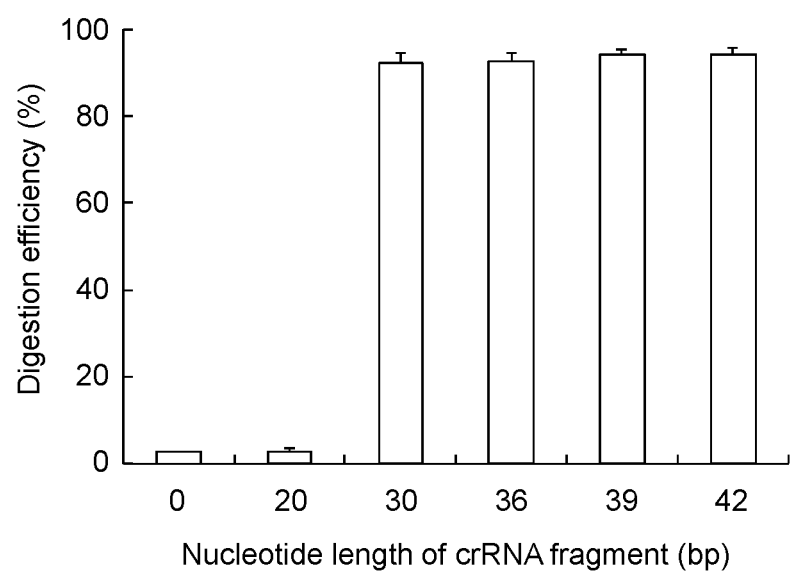

FIG. 3-1 shows the results.

The increase in the digestion efficiency of the PCR product comprising the Actb target sequence depending on the concentrations of the crRNA fragment and the tracrRNA fragment was confirmed. Further, in the case of using 0.61 pmol/μL crRNA and tracrRNA fragments, it was confirmed that the PCR product comprising the Actb target sequence can be cleaved with high efficiency of about 95%.

2. Results of Examination of the crRNA Fragment Length

FIG. 3-2 shows the results.

In the case where the crRNA fragment has a length of 30 bp, that is to say, the case that the fragment contains a 20-bp nucleotide sequence complementary to a target DNA region and a 10-bp nucleotide sequence capable of interacting with a tracrRNA fragment (SEQ ID NO: 9), the cleavage of the PCR product comprising the Actb target sequence with high efficiency of about 95% can be confirmed. This result indicates that, in order to achieve a high level of digestion efficiency, the crRNA fragment may have an at least 20-bp nucleotide sequence complementary to a target DNA region and an at least 10-bp nucleotide sequence capable of interacting with a tracrRNA fragment.

(Preparation of Knock-in Mice)

The crRNA fragment and the tracrRNA fragment were injected in an RNA amount of "0.061 pmol/μL," which is a generally employed amount for the CRISPR/CAS system, together with the Cas9 protein and pActb-TetO-FLEX-EGFP-polyA, into the pronucleus of a fertilized egg. As a result, 9 littermates were obtained. The results of PCR screening of the obtained littermates show that there were no mice having the TetO-FLEX-EGFP-polyA cassette at the Actb locus (Table 4 below).

Figure 4:
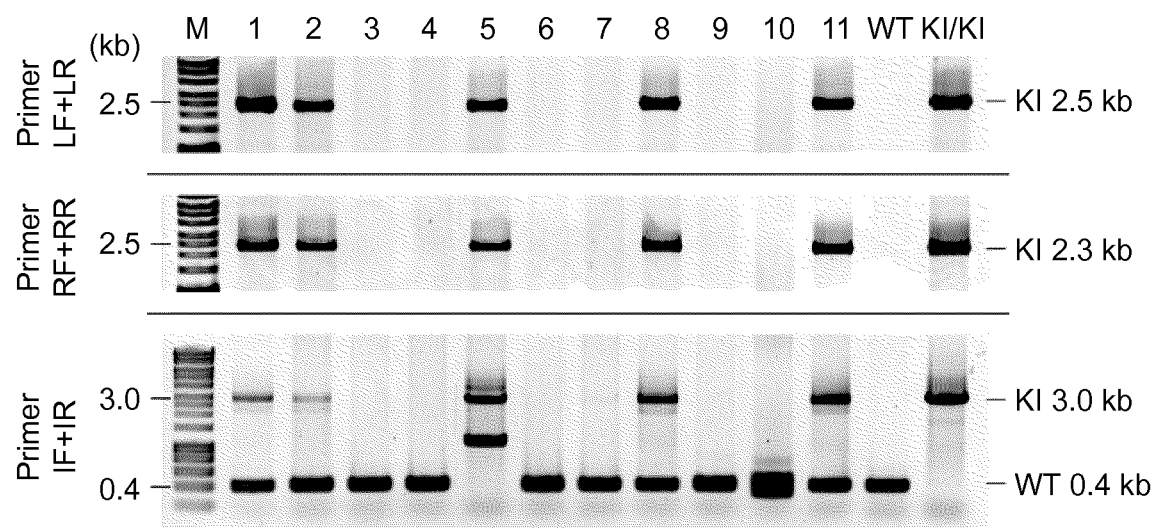
FIG. 4 is a photo showing the results of screening for knock-in mice, indicating that 5 (lanes 1, 2, 5, 8, and 11) out of 11 littermates are knock-in mice.

The injection amounts of the crRNA fragment and the tracrRNA fragment were then increased to "0.61 pmol/μL" and the fragments were injected together with the Cas9 protein and pActb-TetO-FLEX-EGFP-polyA into the pronucleus of a fertilized egg. As a result, 11 littermates were obtained. As a result of PCR screening of the obtained littermates, a very high percentage of the mice (5 mice: 45.5% of all littermates) were confirmed to have the TetO-FLEX-EGFP-polyA cassette at the Actb locus (FIG. 4 and Table 4 below). Some of the obtained knock-in mice were also confirmed to have a homozygous knock-in allele. In other words, it was confirmed that knock-in efficiency can be remarkably improved by increasing the injection amounts of the crRNA fragment and the tracrRNA fragment.

Based on the fact that production efficiency of knock-in mammals in which a gene having a relatively large size has been inserted using the conventional CRISPR-Cas9 system was very low (e.g., about 10% or lower) (Yang, H. et al., ibid.), knock-in efficiency achieved by the present method is considered to be remarkably high.

TABLE 4

| RNA [pmol/μL] | No. of injected fertilized eggs | No. of implanted fertilized eggs (%) | No. of littermates (%) | No. of knock-in mice (%) |
|---|---|---|---|---|
| 0.061 | 67 | 43 (64.2) | 9 (20.9) | 0 (0) |
| 0.61 | 107 | 65 (60.7) | 11 (16.9) | 5 (45.5) |

(Confirmation of the Function of the Knock-in Gene)

Figure 5:
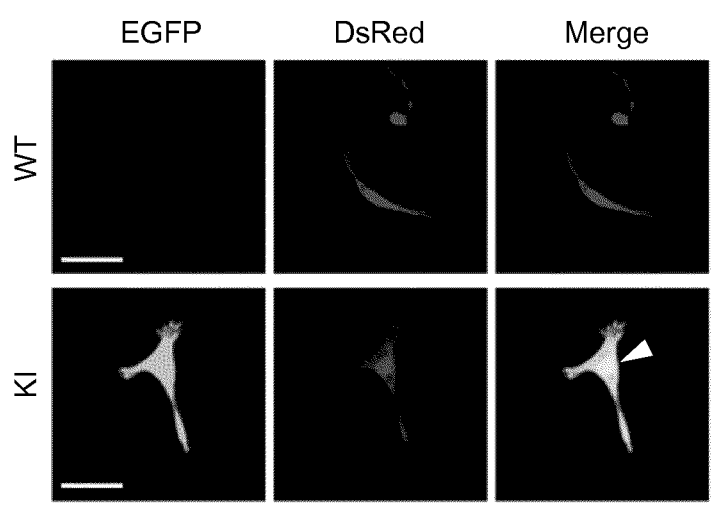
FIG. 5 is a photo showing EGFP expression in fibroblasts derived from knock-in mice. The arrowhead indicates that a region denoted by DsRed and a region denoted by EGFP overlap with each other in knock-in mouse-derived fibroblasts.

Fibroblasts collected from earflaps of the obtained knock-in mice and wild-type mice were separately cultured and cotransfected with pCAG-Cre, pCMV-tTA, and pCMV-DsRed. As a result, fluorescence of EGFP was observed in fibroblasts from the knock-in mice (FIG. 5: arrow head). In particular, strong signals were observed in mice having a homozygous knock-in allele.

This result indicates that functional EGFP was produced from the TetO-FLEX-EGFP-polyA cassette inserted at the Actb locus in the presence of Cre and tTA.

All publications, patents, and patent applications cited herein are incorporated herein by reference in their entirety.

The invention claimed is:

1. A method of producing a knock-in mouse comprising a gene or a nucleotide sequence inserted into a target DNA region, wherein the method comprises introducing a Cas9 protein, a crRNA fragment comprising a nucleotide sequence complementary to the target DNA region, a tracrRNA fragment, and a donor DNA comprising the gene or the nucleotide sequence into a mouse oocyte to insert the gene or the nucleotide sequence into the target DNA region,
   wherein the crRNA fragment has a length of 30 to 42 nucleotides, wherein the tracrRNA fragment has a length of 24 to 69 nucleotides, wherein the Cas9 protein is used at a concentration of 30-500 ng/μL, wherein the crRNA fragment and the tracrRNA fragment are each used at a concentration of 0.6-60 pmol/μL, and
   wherein the size of the gene or the nucleotide sequence to be inserted is 500 bp or more, and wherein the production efficiency of knock-in mouse is 10% or more.

2. The method according to claim 1, wherein the crRNA fragment and the tracrRNA fragment are each used at a concentration of more than 0.02 pmol/μL based on 1 ng/μL Cas9 protein.

3. The method according to claim 1, wherein the crRNA fragment and the tracrRNA fragment are each used at a concentration of 0.6-6 pmol/μL.

4. The method according to claim 2, wherein the crRNA fragment and the tracrRNA fragment are each used at a concentration of 0.6-6 pmol/μL.

5. The method according to claim 1, wherein the Cas9 protein is used at a concentration of 30 ng/μL, wherein the crRNA fragment and the tracrRNA fragment are each used at a concentration of 0.61 pmol/μL, and the donor DNA is used at a concentration of 10 ng/μL.

* * * * *

SEQUENCE LISTING

<160> NUMBER OF SEQ ID NOS: 16

<210> SEQ ID NO 1
<211> LENGTH: 1368
<212> TYPE: PRT
<213> ORGANISM: Streptococcus pyogenes serotype M1

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

-continued

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

-continued

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
            1010                1015                1020

Lys Ser Glu Gln Glu Ile Gly Lys Ala Thr Ala Lys Tyr Phe Phe
            1025                1030                1035

Tyr Ser Asn Ile Met Asn Phe Phe Lys Thr Glu Ile Thr Leu Ala
            1040                1045                1050

Asn Gly Glu Ile Arg Lys Arg Pro Leu Ile Glu Thr Asn Gly Glu

|   |   |   |   |   |   |   |   |   |   |
|---|---|---|---|---|---|---|---|---|---|
|   |   | 1055 |   |   | 1060 |   |   | 1065 |   |
| Thr | Gly | Glu | Ile | Val | Trp | Asp | Lys | Gly | Arg | Asp | Phe | Ala | Thr | Val |
|   |   | 1070 |   |   | 1075 |   |   | 1080 |   |
| Arg | Lys | Val | Leu | Ser | Met | Pro | Gln | Val | Asn | Ile | Val | Lys | Lys | Thr |
|   |   | 1085 |   |   | 1090 |   |   | 1095 |   |
| Glu | Val | Gln | Thr | Gly | Gly | Phe | Ser | Lys | Glu | Ser | Ile | Leu | Pro | Lys |
|   |   | 1100 |   |   | 1105 |   |   | 1110 |   |
| Arg | Asn | Ser | Asp | Lys | Leu | Ile | Ala | Arg | Lys | Lys | Asp | Trp | Asp | Pro |
|   |   | 1115 |   |   | 1120 |   |   | 1125 |   |
| Lys | Lys | Tyr | Gly | Gly | Phe | Asp | Ser | Pro | Thr | Val | Ala | Tyr | Ser | Val |
|   |   | 1130 |   |   | 1135 |   |   | 1140 |   |
| Leu | Val | Val | Ala | Lys | Val | Glu | Lys | Gly | Lys | Ser | Lys | Lys | Leu | Lys |
|   |   | 1145 |   |   | 1150 |   |   | 1155 |   |
| Ser | Val | Lys | Glu | Leu | Leu | Gly | Ile | Thr | Ile | Met | Glu | Arg | Ser | Ser |
|   |   | 1160 |   |   | 1165 |   |   | 1170 |   |
| Phe | Glu | Lys | Asn | Pro | Ile | Asp | Phe | Leu | Glu | Ala | Lys | Gly | Tyr | Lys |
|   |   | 1175 |   |   | 1180 |   |   | 1185 |   |
| Glu | Val | Lys | Lys | Asp | Leu | Ile | Ile | Lys | Leu | Pro | Lys | Tyr | Ser | Leu |
|   |   | 1190 |   |   | 1195 |   |   | 1200 |   |
| Phe | Glu | Leu | Glu | Asn | Gly | Arg | Lys | Arg | Met | Leu | Ala | Ser | Ala | Gly |
|   |   | 1205 |   |   | 1210 |   |   | 1215 |   |
| Glu | Leu | Gln | Lys | Gly | Asn | Glu | Leu | Ala | Leu | Pro | Ser | Lys | Tyr | Val |
|   |   | 1220 |   |   | 1225 |   |   | 1230 |   |
| Asn | Phe | Leu | Tyr | Leu | Ala | Ser | His | Tyr | Glu | Lys | Leu | Lys | Gly | Ser |
|   |   | 1235 |   |   | 1240 |   |   | 1245 |   |
| Pro | Glu | Asp | Asn | Glu | Gln | Lys | Gln | Leu | Phe | Val | Glu | Gln | His | Lys |
|   |   | 1250 |   |   | 1255 |   |   | 1260 |   |
| His | Tyr | Leu | Asp | Glu | Ile | Ile | Glu | Gln | Ile | Ser | Glu | Phe | Ser | Lys |
|   |   | 1265 |   |   | 1270 |   |   | 1275 |   |
| Arg | Val | Ile | Leu | Ala | Asp | Ala | Asn | Leu | Asp | Lys | Val | Leu | Ser | Ala |
|   |   | 1280 |   |   | 1285 |   |   | 1290 |   |
| Tyr | Asn | Lys | His | Arg | Asp | Lys | Pro | Ile | Arg | Glu | Gln | Ala | Glu | Asn |
|   |   | 1295 |   |   | 1300 |   |   | 1305 |   |
| Ile | Ile | His | Leu | Phe | Thr | Leu | Thr | Asn | Leu | Gly | Ala | Pro | Ala | Ala |
|   |   | 1310 |   |   | 1315 |   |   | 1320 |   |
| Phe | Lys | Tyr | Phe | Asp | Thr | Thr | Ile | Asp | Arg | Lys | Arg | Tyr | Thr | Ser |
|   |   | 1325 |   |   | 1330 |   |   | 1335 |   |
| Thr | Lys | Glu | Val | Leu | Asp | Ala | Thr | Leu | Ile | His | Gln | Ser | Ile | Thr |
|   |   | 1340 |   |   | 1345 |   |   | 1350 |   |
| Gly | Leu | Tyr | Glu | Thr | Arg | Ile | Asp | Leu | Ser | Gln | Leu | Gly | Gly | Asp |
|   |   | 1355 |   |   | 1360 |   |   | 1365 |   |

<210> SEQ ID NO 2
<211> LENGTH: 10
<212> TYPE: RNA
<213> ORGANISM: Artificial
<220> FEATURE:
<223> OTHER INFORMATION: synthetic oligonucleotide

<400> SEQUENCE: 2
guuuuagagc                                                          10

<210> SEQ ID NO 3
<211> LENGTH: 22
<212> TYPE: RNA
<213> ORGANISM: Artificial

```
<220> FEATURE:
<223> OTHER INFORMATION: synthetic oligonucleotide

<400> SEQUENCE: 3
guuuuagagc uaugcuguuu ug                                              22

<210> SEQ ID NO 4
<211> LENGTH: 24
<212> TYPE: RNA
<213> ORGANISM: Artificial
<220> FEATURE:
<223> OTHER INFORMATION: synthetic oligonucleotide

<400> SEQUENCE: 4
gcaaguuaaa auaaggcuag uccg                                            24

<210> SEQ ID NO 5
<211> LENGTH: 69
<212> TYPE: RNA
<213> ORGANISM: Artificial
<220> FEATURE:
<223> OTHER INFORMATION: synthetic oligonucleotide

<400> SEQUENCE: 5
aaacagcaua gcaaguuaaa auaaggcuag uccguuauca acuugaaaaa guggcaccga     60
gucggugcu                                                             69

<210> SEQ ID NO 6
<211> LENGTH: 42
<212> TYPE: RNA
<213> ORGANISM: Artificial
<220> FEATURE:
<223> OTHER INFORMATION: synthetic oligonucleotide

<400> SEQUENCE: 6
cauuaugagu ccuuaaguga guuuuagagc uaugcuguuu ug                        42

<210> SEQ ID NO 7
<211> LENGTH: 39
<212> TYPE: RNA
<213> ORGANISM: Artificial
<220> FEATURE:
<223> OTHER INFORMATION: synthetic oligonucleotide

<400> SEQUENCE: 7
cauuaugagu ccuuaaguga guuuuagagc uaugcuguu                            39

<210> SEQ ID NO 8
<211> LENGTH: 36
<212> TYPE: RNA
<213> ORGANISM: Artificial
<220> FEATURE:
<223> OTHER INFORMATION: synthetic oligonucleotide

<400> SEQUENCE: 8
cauuaugagu ccuuaaguga guuuuagagc uaugcu                               36

<210> SEQ ID NO 9
<211> LENGTH: 30
<212> TYPE: RNA
<213> ORGANISM: Artificial
<220> FEATURE:
<223> OTHER INFORMATION: synthetic oligonucleotide

<400> SEQUENCE: 9
```

```
cauuaugagu ccuuaaguga guuuuagagc                                    30

<210> SEQ ID NO 10
<211> LENGTH: 20
<212> TYPE: RNA
<213> ORGANISM: Artificial
<220> FEATURE:
<223> OTHER INFORMATION: synthetic oligonucleotide

<400> SEQUENCE: 10
cauuaugagu ccuuaaguga                                               20

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
tgcagagaac actggttggt                                               20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
caagctaacc tcagccttgc                                               20

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
tccctggaga agagctatga                                               20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
tataggcctc ccaccgtaca                                               20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
gagtgcagtg gcacaatctt                                               20

<210> SEQ ID NO 16
<211> LENGTH: 24
<212> TYPE: DNA
<213> ORGANISM: Artificial
```

```
<220> FEATURE:
<223> OTHER INFORMATION: primer

<400> SEQUENCE: 16
ccagatgcct tctgttgcat gctt                                              24
```